United States Patent [19]

Friedman

[11] Patent Number: 4,948,215

[45] Date of Patent: Aug. 14, 1990

[54] DENTAL LIGHT-CURING LAMP UNIT WITH INTERCHANGEABLE AUTOFOCUS LIGHT GUIDES

[76] Inventor: Joshua Friedman, 13 Fairfield Ct., Ridgefield, Conn. 06877

[21] Appl. No.: 392,023

[22] Filed: Aug. 10, 1989

[51] Int. Cl.⁵ .............................................. G02B 6/14
[52] U.S. Cl. .............................. 350/96.10; 250/504 R; 433/229
[58] Field of Search ............... 350/96.10, 96.20, 96.26; 362/32; 433/229; 250/50 HH

[56] References Cited

U.S. PATENT DOCUMENTS

| | | | |
|---|---|---|---|
| 3,868,513 | 2/1975 | Gonser | 250/504 H |
| 4,298,806 | 11/1981 | Herold | 250/504 H |
| 4,666,406 | 5/1987 | Kanca, III | 433/229 |
| 4,792,692 | 12/1988 | Herold et al. | 350/96.10 X |
| 4,797,101 | 1/1989 | Morris | 433/229 |

Primary Examiner—William L. Sikes
Assistant Examiner—Phan T. Heartney

[57] ABSTRACT

Assembly of interchangeable autofocus light guides of varying diameter for a dental curing light apparatus to provide maximum power density independently of the selection of light guide. Each light guide has an optic rod of a preselected diameter and a proximal end axially spaced from the focal spot, such that radiant energy incident upon the proximal end corresponds to a predetermined surface area matched to said preselected diameter. Each optic rod also has a head of common diameter for interchangeable insertion into the light-curing apparatus.

5 Claims, 3 Drawing Sheets

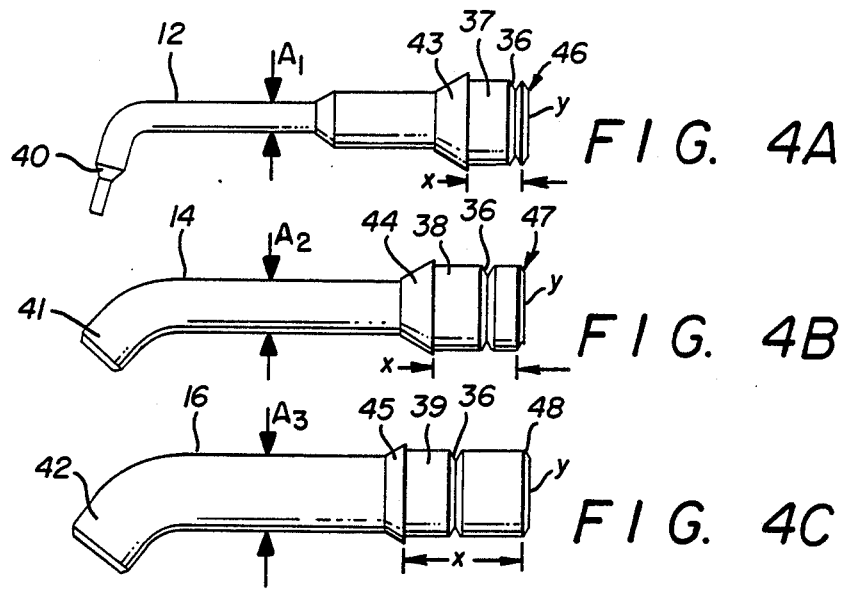
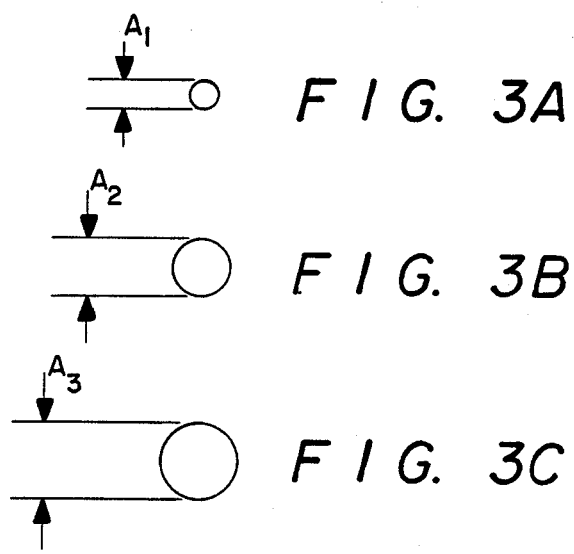

DENTAL LIGHT-CURING LAMP UNIT WITH INTERCHANGEABLE AUTOFOCUS LIGHT GUIDES

FIELD OF THE INVENTION

This invention relates to an assembly of plural interchangeable autofocus light guides of varying diameters for a dental curing light apparatus to provide maximum power density independently of the selection of light guide.

BACKGROUND OF THE INVENTION

Photocurable dental materials are cured by exposure to radiant energy in a preselected spectral range in either the ultraviolet or visible spectrum. The materials are used by dentists intraorally as a replacement for gold, porcelain, or silver amalgam to fill cavities and to repair chipped or broken teeth, as well as to coat teeth for cosmetic reasons. The radiant energy is transmitted from a lamp in a lamp assembly through an optic light guide. To subject the dental material to the maximum available light energy, the distal end of the optic light guide is positioned as close as possible to the photocurable material in the dental restoration. Best results are achieved when the light is uniformly applied over the entire surface area of the material to be cured. However, the surface area varies with the size of the restoration and is, in general, larger for posterior restorations, as compared with anterior restorations. In addition, small diameter light guides are generally required to reach areas which would otherwise be inaccessible, such as the gingival floor of posterior restorations. Accordingly, maximum power distribution and intensity, i.e., power density is assured when the surface area is matched to the optics of the light curing unit.

The foregoing is accomplished in accordance with the present invention using a light curing assembly and a plurality of interchangeable autofocus light guides having preselected diameters corresponding to typical surface area variations and a matched preselected length to provide optimum spacing relative to the focal point of the curing lamp. The autofocus light guides are adapted to be interchangeably inserted into the light-curing assembly to provide maximum power density independently of the selection of the autofocus light guide.

SUMMARY OF THE INVENTION

Assembly of interchangeable autofocus optic light guides for a dental light-curing unit having a housing for a source of radiant energy, a reflector partially surrounding said source of energy so as to converge reflected radiant energy to a preselected focal spot along a preselected optic axis and chuck means for holding an autofocus light guide in a fixed position along said optic axis upon insertion into said chuck means, with each auto focus optic light guide comprising an optic rod of a diameter corresponding to a preselected photocurable surface area with a proximal end for forming a light-receiving surface for incident radiant energy reflected from said lamp with said proximal end being spaced from the focal spot such that the radiant energy incident upon said light-receiving surface corresponds to said preselected photocurable surface area and with each optic rod having a head surrounding the proximal end thereof with a common diameter for insertion into said chuck means.

BRIEF DESCRIPTION OF THE DRAWING

Further advantages of the invention will become apparent from the following detailed description of the invention when read in conjunction with the accompanying drawings of which:

FIG. 3A is a view taken along lines 3A—3A of FIG. 2 showing the surface area of the light beam at the plane of intersection with lines 3A—3A;

FIG. 3B is a view taken along lines 3B—3B of FIG. 2 showing the surface area of the light beam at the plane of intersection with lines 3B—3B;

FIG. 3C is a view taken along lines 3C—3C of FIG. 2 showing the surface area of the light beam at the plane of intersection with lines 3C—3C;

FIG. 4A is a side elevation of a first autofocus light guide in accordance with the present invention for providing an effective light-transmitting surface area equal to the surface area of FIG. 3A;

FIG. 4B is a side elevation of a second autofocus light guide in accordance with the present invention for providing an effective light-transmitting surface area equal to the surface area of FIG. 3B;

FIG. 4C is a side elevation of a third autofocus light guide in accordance with the present invention for providing an effective light-transmitting surface area equal to the surface area of FIG. 3C;

DESCRIPTION OF THE PREFERRED EMBODIMENT

Figure 1:
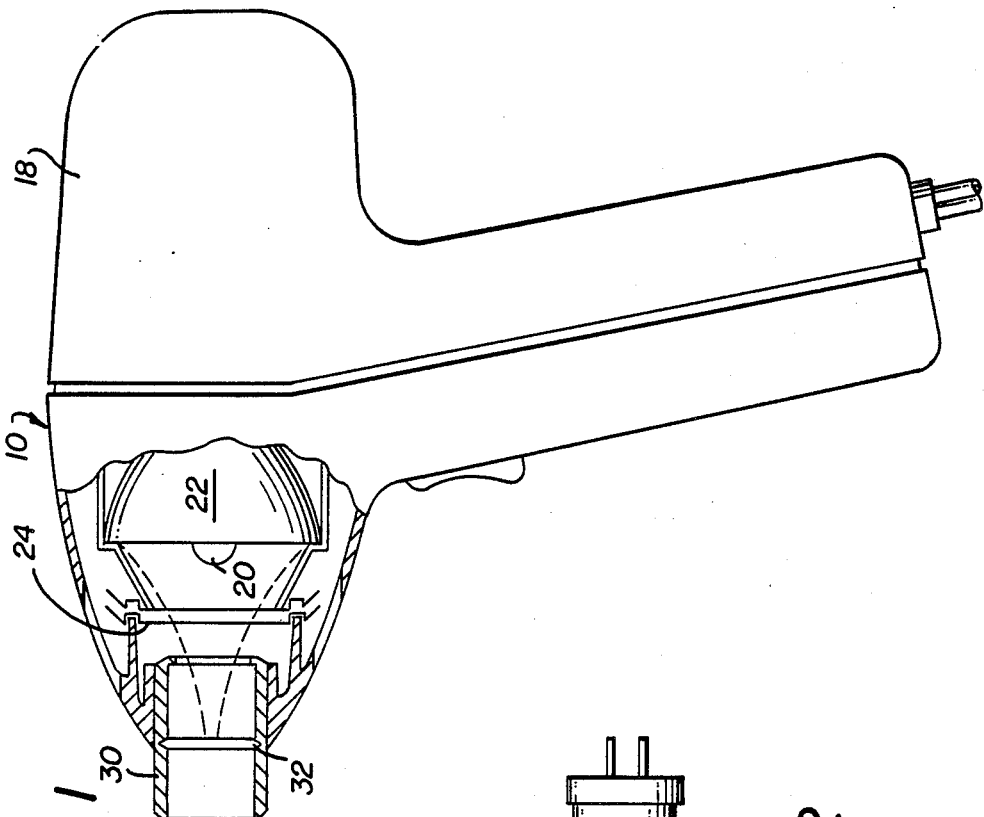
FIG. 1 is a longitudinal view partially in section of a hand-held dental light-curing unit for securing an autofocus light guide in accordance with the present invention.
Figure 1A:
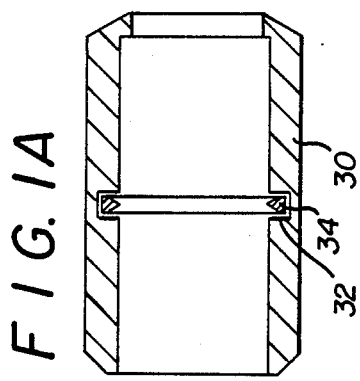
FIG. 1A is an enlarged cross-sectional view of the chuck assembly of FIG. 1.

A hand-held dental light-curing unit (10), as shown in FIG. 1, is used in combination with an optic light guide selected from a plurality of autofocus optic light guides (12), (14), and (16), as shown in FIGS. 4A, 4B and 4C, respectively, for transmitting light to photocurable dental material (not shown) at a site external of the light-curing unit (10). In accordance with the present invention, maximum power density is applied to the dental material from the light-curing unit (10) independently of the selection of autofocus optic light guide (12), (14), or (16), respectively.

Figure 2:
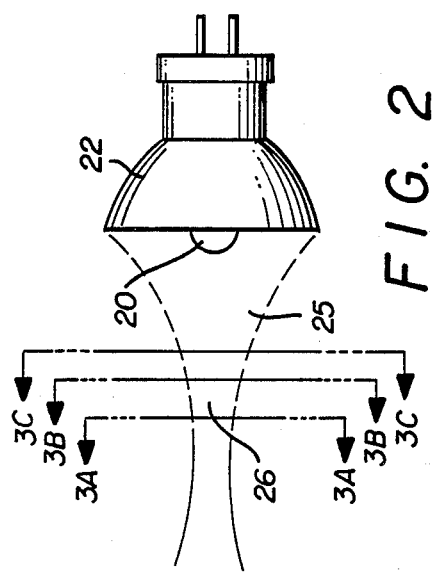
FIG. 2 is a diagrammatic illustration of the reflected radiant energy distribution profile for the lamp in the light-curing unit of FIG. 1.
Figure 5A:
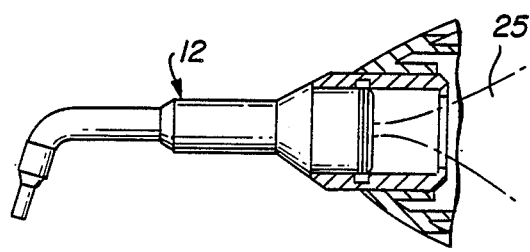
FIG. 5A is a side elevation of the first autofocus light guide of FIG. 4A shown in the inserted position in the chuck of the dental light-curing unit of FIG. 1.
Figure 5B:
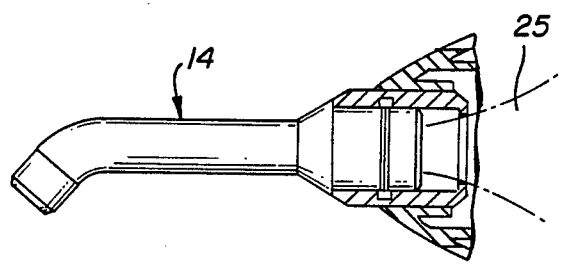
FIG. 5B is a side elevation of the second autofocus light guide of FIG. 4B shown in the inserted position in the chuck of the dental light-curing unit of FIG. 1.
Figure 5C:
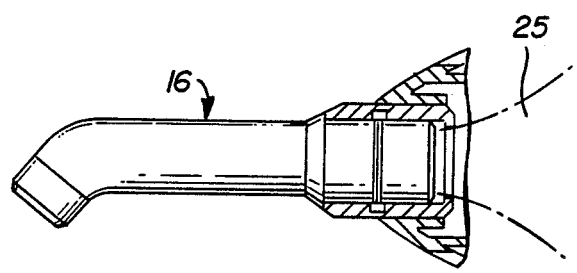
FIG. 5C is a side elevation of the third autofocus light guide of FIG. 4C shown in the inserted position in the chuck of the dental light-curing unit of FIG. 1.

The hand-held dental light-curing unit (10) includes a housing (18) containing a source of radiant energy, such as a halogen lamp (20), a reflector (22) for the lamp (20), and a suitable filter or filter assembly (24). The lamp (20) may be of the tungsten/halogen type, or of the mercury vapor, short arc xenon, or metal halide type, dependent upon the desired spectral bandwidth of radiant energy. The filter assembly (24) is spaced apart from the lamp (20) along the optic axis for filtering unwanted light energy. The reflector (22) has an elliptical shape and is mounted behind the lamp (20) for reflecting and focusing light energy generated from the lamp. The reflected radiant energy profile for the lamp (20) is shown in FIG. 2. For a typical size halogen lamp (20), the light energy beam (25) converges to a focal spot (26) and then begins to diverge. The light beam (25) has a distinct surface area at any given position along the optic axis which can be mathematically calculated. Three specific surface areas (A1), (A2), and (A3), are shown in FIGS. 3A to 3C, corresponding to the plane of intersection of lines (3A), (3B), and (3C) through the light beam (25) of FIG. 2.

The dental light-curing unit (10) of FIG. 1 includes a bushing (30) in the form of a chuck for removably receiving any one of the autofocus light guides (12), (14), and (16) of FIG. 4. The bushing (30) has a circular groove (32) with a split ring (34) which snaps over a complementary circular groove (36) in the head (37), (38), and (39) of each of the autofocus light guides (12), (14), and (16), so as to removably hold the inserted light guide in a fixed position along the optic axis. Each of the autofocus light guides (12), (14), and (16) may be composed of glass, quartz, or plastic fiber optic rod, or other light-conducting medium of any preferred length. Each optic light guide (12), (14), and (16) is generally 3 to 4 inches in length and has a contoured tip (40), (41), and (42) at the distal end thereof. The maximum surface area through which light can be transmitted through each light guide corresponds to the surface areas (A1), (A2), and (A3) of FIGS. 3A, 3B and 3C, respectively.

The head (37), (38) and (39) of each light guide is cylindrical in geometry and equivalent in diameter to one another with each head corresponding to the internal diameter of the bushing (30) into which it is removably inserted. Each head has a chamfered flange (43), (44) and (45) which engages the bushing (30) upon insertion of the head. The proximal end (46), (47), and (48) of each optic light guide (12), (14), and (16), respectively, forms a light-receiving surface ("y") for receiving incident radiant energy reflected from the lamp (20). The axial dimension ("x") represents the distance from each flange (43), (44), and (45) to the light-receiving surface, identified as "y" at the proximal end (46), (47), and (48) of each light guide (12), (14), and (16), respectively. The distance "x") is preselected such that the surface area of incident light at the receiving surface ("y") corresponds to the surface areas (A1), (A2) and (A3) of FIGS. 3A, 3B, and 3C, respectively. The surface areas (A1), (A2), and (A3) correspond to the surface areas formed by the planes of intersection (3A—3A), (3B—3B), and (3C—3C) with the light beam, as shown in FIG. 2, and match the surface areas of the optic light guides (12), (14) and (16). Thus maximum power density is realized independently of the selection of the optic light guide.

I claim:

1. Assembly of a plural number of interchangeable autofocus optic light guides for use in a single dental light-curing unit having a housing for a source of radiant energy such as a lamp, a reflector partially surrounding said source of energy so as to converge reflected radiant energy to a preselected focal spot along a preselected optic axis and chuck means adapted to hold a single autofocus light guide in a fixed position along said optic axis upon insertion into said chuck means, with each into focus optic light guide comprising an optic rod of a diameter corresponding to a preselected photocurable surface area with the diameter of each rod being different from one another, a flange surrounding each rod adjacent one end thereof for abutting said chuck means in the inserted position and for establishing a fixed position for each rod relative to the preselected focal spot and wherein each rod has a proximal end for forming a light-receiving surface for incident radiant energy reflected from said lamp with the proximal end of each rod being spaced a predetermined distance from the position of each flange such that the surface area of radiant energy incident upon said light-receiving surface corresponds to the diameter of the optic rod independent of the light guide selected and with each optic rod having a head surrounding the proximal end thereof with said flange extending from said head and means for removably inserting the head into said chuck means.

2. Assembly, as defined in claim 1, wherein each head has a common diameter for insertion into said chuck means.

3. Assembly, as defined in claim 2, wherein said means for insertion of each head into said chuck means comprises a circular groove disposed about the head of each rod and a chamfered flange at one end of each head to engage said chuck means, with the distance between said circular groove and said flange being substantially equivalent for each light guide.

4. Assembly, as defined in claim 3, wherein said chuck means of said dental light-curing unit comprises a bushing and includes means for removably coupling the bushing into the circular groove of an optic rod.

5. Assembly, as defined in claim 3, wherein said removable coupling means is a split ring.

* * * * *